United States Patent [19]
Light et al.

[11] Patent Number: 5,764,721
[45] Date of Patent: Jun. 9, 1998

[54] METHOD FOR OBTAINING OPTIMIZED COMPUTED TOMOGRAPHY IMAGES FROM A BODY OF HIGH LENGTH-TO-WIDTH RATIO USING COMPUTER AIDED DESIGN INFORMATION FOR THE BODY

[75] Inventors: Glenn M. Light, San Antonio, Tex.; Daniel Schneberk, Manteca, Calif.

[73] Assignee: Southwest Research Institute, San Antonio, Tex.

[21] Appl. No.: 780,745

[22] Filed: Jan. 8, 1997

[51] Int. Cl.$^6$ ............................................. A61B 6/03
[52] U.S. Cl. ................................. 378/4; 378/8; 378/16
[58] Field of Search ........................ 378/4, 8, 19, 16, 378/95

[56] References Cited

U.S. PATENT DOCUMENTS

| | | | |
|---|---|---|---|
| 4,065,397 | 12/1977 | Ruhrnschopf | 250/445 |
| 4,293,912 | 10/1981 | Walters | 364/414 |
| 4,303,829 | 12/1981 | Wagner | 378/8 X |
| 4,506,327 | 3/1985 | Tam | 364/414 |
| 4,920,491 | 4/1990 | Eberhard | 364/413 |
| 4,969,110 | 11/1990 | Little | 364/550 |
| 5,023,895 | 6/1991 | McCroskey | 378/4 |
| 5,103,469 | 4/1992 | Tanaka | 378/16 |
| 5,138,642 | 8/1992 | McCroskey | 378/19 |
| 5,400,378 | 3/1995 | Toth | 378/16 |
| 5,450,462 | 9/1995 | Toth et al. | 378/16 |

*Primary Examiner*—David P. Porta
*Attorney, Agent, or Firm*—Kammer & Huff, PLLC

[57] ABSTRACT

An apparatus and method for optimizing computer tomography images obtained from any of a number of different standard computer tomography scanning devices. The apparatus and method incorporate computer-aided design data for an object being scanned into a system for establishing nominal scanning beam intensities and nominal scanning detector sensitivities that ultimately compensate for non-anomalous variations in beam path characteristics. Particularly adapted for optimizing scan images on objects with large length-to-width ratios, the present invention identifies significant deviations from some normal baseline beam path in advance of a scan and modifies beam intensity and detector sensitivity to bring the projected beam into a nominal range. Thereafter, deviations from this referenced nominal beam can be better identified as anomalies within the object being scanned, that are of interest.

6 Claims, 7 Drawing Sheets

METHOD FOR OBTAINING OPTIMIZED COMPUTED TOMOGRAPHY IMAGES FROM A BODY OF HIGH LENGTH-TO-WIDTH RATIO USING COMPUTER AIDED DESIGN INFORMATION FOR THE BODY

BACKGROUND OF THE INVENTION

1. Field of the Invention

The present invention relates generally to methods and devices for imaging internal cross sectional views of objects or bodies under inspection. The present invention relates more specifically to a method and apparatus for improving the dimensional measurement capabilities of computer tomography images from bodies with high length-to-width ratios through the use of computer aided design technologies and other information on the object under inspection.

2. Description of the Prior Art

X-ray tomography was developed early on in the 1930's using standard photographic film as a recording medium for the X-ray images. More recently, through the use of electronic photon detectors, more advanced detection systems, and more advance computer technology, X-ray tomographic images can be created by computing the attenuation of X-ray paths through the material or object under inspection. This technology, now referred to as "computer tomography" or simply "CT," is well known in the field and is frequency utilized for obtaining internal, cross sectional images of the human body in medical applications.

The purpose of CT is to reconstruct an image that reproduces the internal cross section of the body under inspection. Electronic photon detectors can collect a large amount of data that represents the attenuation of a well collimated X-ray beam that passes at a number of different angles through all points within the cross sectional area being imaged. Frequently referred to as a "CT scan", the direction of the X-ray beam is varied through a controlled sweep and information on the passage of X-ray photons through the body under inspection is collected for each area of the scan. The data collected is then processed by a computer to reconstruct the image of the cross section under inspection through the performance of a series of mathematical operations and algorithms. The processor outputs an array of numbers that represent the linear X-ray attenuation co-efficient for a small volume element (referred to as a voxel) within the cross section slice under inspection. An even larger group of these arrays of numbers are assembled to form the entire cross sectional image desired. These numbers are then converted into an image using a gray or color scale conversion that finally produces an image of the cross section under inspection with visual features predetermined by the image conversion process to exhibit those physical features of concern.

The various technologies that permitted the development and creation of a CT image are 1) the ability to create a highly collimated X-ray beam, 2) technology to create very sensitive signal-to-noise detectors for X-ray photons, 3) detector technology that allows the sensors to be read and refreshed quickly so that nearly continuous X-ray beam intensity measurements can be obtained, 4) the development of programs that include algorithms for handling large amounts of data through the use of arrays and imaging technologies, 5) computer processor technology with the capability to perform calculations for the determination of linear attenuation co-efficients for each voxel under examination, and finally 6) the development of display technology that allows the attenuation co-efficients to be shown in shades of gray or color according to preselected patterns and choices depending upon the application.

CT technology has been used frequently over the last 10–15 years to image the cross sectional densities of objects that range from human bodies as in medical applications, to large diameter solid rocket motors in engineering type applications. In most cases where CT technology accomplishes highly accurate imaging, the object being inspected will have a near cylindrical shape. The reason cylindrical shapes create the optimum case for CT technology is because such shapes do not exhibit a wide disparity in the linear attenuation co-efficients that are seen by the X-ray beam during the inspection. The cylindrical cross section makes the reconstruction process and X-ray beam energy selection reasonably straight forward. However, when the object under inspection has a wide range of attenuation co-efficiency, it becomes difficult to optimize the X-ray beam energy so as to develop a reconstructed image that has nominally uniform contrast and resolution.

Conventional CT technology employs a single source of X-rays usually of a given energy or energy spectrum and directs the X-ray beam so as to pass through the body being inspected into an array of X-ray photon detectors. Most commonly, the X-ray source and the detectors are fixed relative to each other and are rotated around the body to collect data for various passes through the body as they rotate. In medical applications, such CT scanning devices are the familiar donut shaped scanners through which the patience body is passed and the donut is rotated to complete the scan.

A first method of data collection in such applications involves progressively directing a set of line rays through the body that are decreased in intensity due to the absorption of the X-rays by the body. In refined applications of this technology, the scan is the combination of a rotational movement and a linear translation of the X-ray source and crystal X-ray photon detector across a path that approximates the diameter of the cylinder of the object under investigation. The linear scan across the diameter of the object is repeated after the entire system has been rotated a small radial increment, eventually through a total of 90 degrees. A first translation of the X-ray tube/crystal detector pair, for example, would be made horizontally across the object under inspection and one degree rotational increments would tilt this inspection angle through to the point whereon the 91st translation, the X-ray tube crystal detector pair scan a vertical line through the cylindrical object under inspection.

A second method of application of the technology utilize a source that creates an intentionally less collimated X-ray path and directs the X-ray beam at an array of detectors rather than a single detector after passing through the object under inspection. Such devices allow greater increments in the rotational movement of the system and thus speed up the overall imaging procedure. The example given above of a process through 90 degrees would, instead of requiring 90 rotational increments, perhaps require only 16 rotational increments.

A third technology incorporates a single source X-ray tube and an even larger array of detectors opposite the tube across the object under inspection. Again, the X-ray beam is intentionally non-collimated and is directed so as to intersect the body under inspection and to impinge upon a semi-circular array of the detectors opposite. The entire X-ray tube/detector array assembly is simply rotated about the object under inspection on a continuous basis to create a large array of absorption path values.

Finally, a fourth typical application of the technology utilizes a single X-ray tube as a source of X-rays that rotates 360 degrees about the object under inspection and impinges upon a non-rotating cylindrical array of detectors that collects the data. This last system for implementing CT technology works quite well, but requires a much larger, typically expensive array of detectors.

As indicated, each of the applications of CT technology described above depends upon the simplicity associated with a cylindrical body under inspection. Significant deviations from the cylindrical shape prevent the system from accurately analyzing the attenuation or the absorption for each particular X-ray beam. The accumulation of data and the structured association of one bit of data for a particular X-ray beam and path, with a second bit of data for a second X-ray beam and path is complicated enough without adding to it external factors such as changes in the basic attenuation of the object under investigation due to significant differences in the cross sectional diameter of the object.

The basis of the present application of this technology is the assumption that the attenuation or absorption of the X-ray beam when it passes through the object under investigation is due to changes in the internal characteristics of the object and not due to significant differences in the total path length through the object that the X-ray beam must travel. For example, with an object of a generally cylindrical structure, such as the human body that might have a cross sectional diameter on the order of 50 cm, the length-to-width ratio is usually quite small, typically three-to-two or below. When the length-to-width ratio, however, exceeds two-to-one or three-to-one, the effects of attenuation due to path length through the body become much more significant. Failure to take into account the attenuation that is due to path length would result in entirely erroneous attenuation or absorption values.

As an example, one typical application of conventional CT technology is in the analysis of turbine blade cross sections for fatigue, internal cracks, voids, delaminations, etc. The typical turbine blade is very long in one cross sectional direction and very short in the other. Having the cross sectional shape of an aerodynamic wing, the length-to-width ratio could be on the order of as much as eight or ten-to-one. If such a turbine blade after use began to develop a number of internal fatigue cracks or voids, it would be desirable to accurately and clearly detect and determine the location of these voids in the accurate analysis of such fatigue testing.

Under conventional CT technology, an array of minute voids or internal fractures could be shown as a single large internal void or fracture because of the great variations in the path of the X-rays as they pass through the cross sectional area of the turbine blade. As an example, an X-ray beam that passes through the length of the turbine blade would show a significant attenuation regardless of what internal features it had to pass through. The long internal path it must take before reaching the detector results in a signal attenuation that depends more upon the length dimension than upon the internal structures through which it passes. A high attenuation, therefore, could be erroneously interpreted as the absence of any voids or internal fractures along that path of the X-ray beam. Likewise, an X-ray beam that passes through the more narrow width of the turbine blade might have a very low attenuation, despite the fact that no voids or internal fractures were encountered along the path. Such low attenuation could be erroneously interpreted as the existence of a large internal void or fracture within the turbine blade in that area of the inspection.

It can be seen, therefore, that current CT technology can result in wholly inappropriate views or images of the internal structures of objects that radically depart from the standard cylindrical cross sectional configuration.

It would be desirable to somehow compensate for high length-to-width object ratios and still be able to use the advantages of CT technology for the inspection of non-cylindrical objects.

To overcome some of these limitations, a number of systems have been developed that employ dual energy CT scanners that actually produce two reconstructed images, one that is optimized for one part of the body under inspection and a second that is optimized for another part of the body. In other words, these systems utilize the same array of detectors and simply allowing them to measure X-ray beam intensities from two different sources that are calculated to compensate for changes in the structure of the object under inspection. The dual system effectively pulls down or pushes up the numbers being gathered based upon a rough guess as to the variations in the cylindrical cross section of the object. Such systems, however, have not been completely satisfactory, especially when the body under inspection has an aspect ratio approaching five to ten. It would be desirable, therefore, to utilize CT technology to reconstruct images of non-cylindrical bodies whose aspect ratios are quite high and to thereby produce images that have a nominal contrast and resolution throughout so as to permit accurate interpretation of the information when presented to the test operator.

SUMMARY OF THE INVENTION

It is therefore an object of the present invention to provide an improved process for obtaining optimized computed tomography images from a body that has a high length-to-width ratio through the use of computer aided design information already established for the body.

It is a further object of the present invention to provide a process for obtaining optimized CT images from a body with high length-to-width ratios by compensating for and taking into consideration the changes in the X-ray beam path typically traveled by conventional CT technology scanners.

It is another object of the present invention to provide a process for optimizing CT images gathered by conventional CT devices through the addition of CAD information on the cross sectional areas of the objects under investigation.

It is a further object of the present invention to provide a process for optimizing CT images from a number of different standard CT scanning devices that include both single source detector devices and multiple source and detector array type devices.

In fulfillment of these and other objects, the present invention provides a method of using information on the basic geometry of an object under investigation in a CT scan through the use of previously accumulated computer aided design data and the coordination of this data with data collected from the CT scan. The process of the present invention utilizes large CAD data files that describe the internal structure of each specific object under inspection for example a turbine blade, which provide information about the total object path for each X-ray beam through the object. The process takes into consideration all of the various parameters that effect the quality of a CT image in terms of contrast, sensitivity, and spatial resolution. With this information and with the ability to modify the X-ray energy of the source or the detector integration time, an optimum set of parameters can be determined. With accurate information not only on the dimensional characteristics of the blade or object being inspected, but also an understanding of the material that the object is constructed of and the attenuation effects that the material has, a thorough understanding of the interaction of these factors with the overall linear attenuation of an X-ray passing through the object can be made. From this information, a scan plan for the object under inspection can be created. This procedural plan would incorporates variations in the X-ray energy and in the detector integration time that are controlled according to the prior knowledge of the expected X-ray path and theoretical attenuation co-efficients based upon some nominal characteristics of the object through that path. The present invention combines computerized physical description of the object and a thorough understanding of the material that the object is constructed of with computerized control of the integration time of the detector array and computerized control of the X-ray energy being transmitted. Other objects and advantages of the method of the present invention will be seen from a description of a preferred embodiment outlined below and from the appended claims.

BRIEF DESCRIPTION OF THE DRAWINGS

FIG. 3b is a cross sectional image that would be created by prior art CT technology of the cross sectional view shown in FIG. 3a.

FIG. 3c is a cross sectional image that would be created by the process of the present invention of the cross-sectional view shown in FIG. 3a.

FIG. 6 is a plot of sample X-ray transmission values for different beam path lengths as a function of beam energy.

DESCRIPTION OF THE PREFERRED EMBODIMENT

Figure 1:
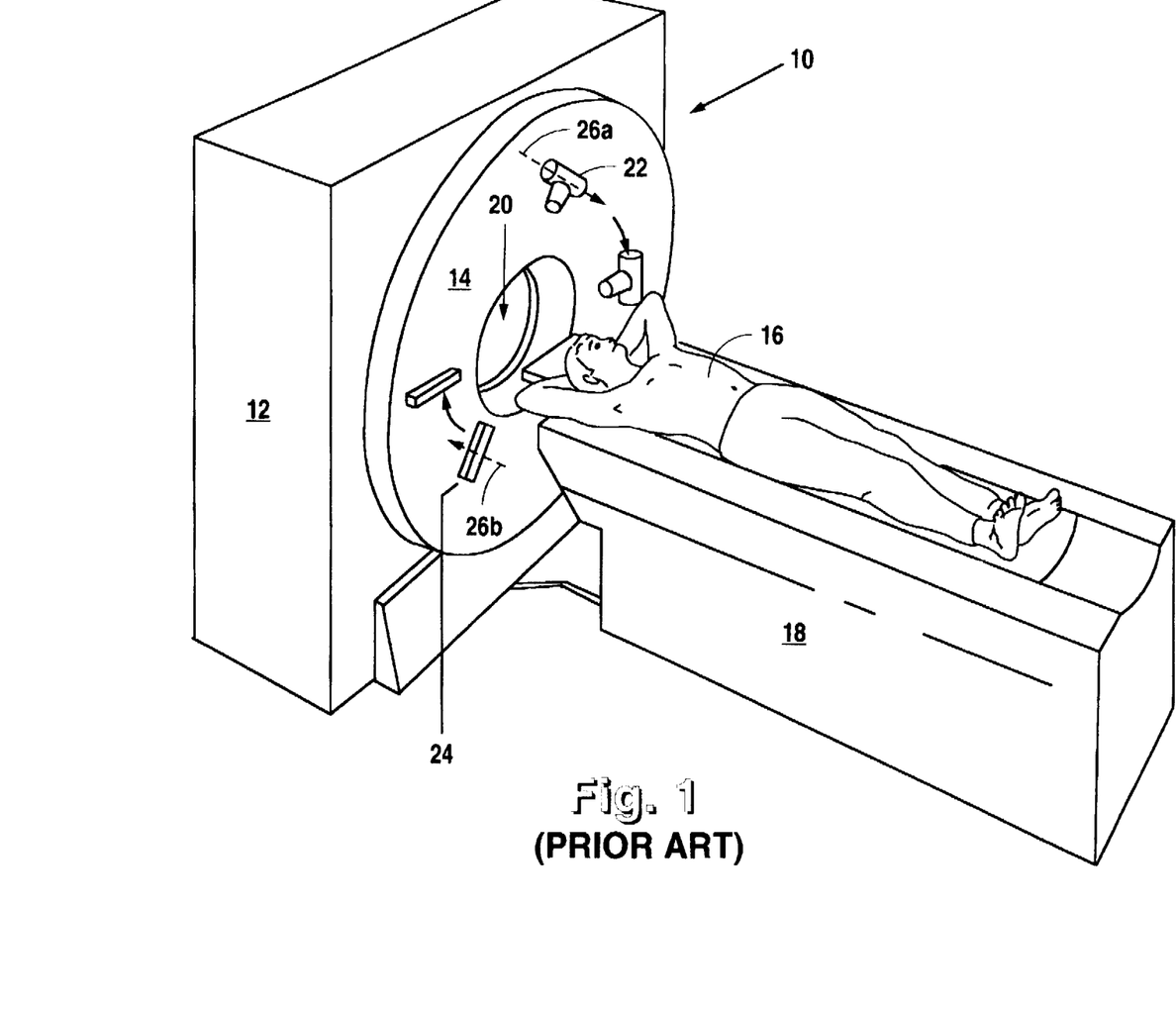
FIG. 1 is a perspective view of a prior art configuration of the application of conventional computed tomography (CT) as it is applied in medical research.

Reference is made first to FIGS. 1 and 2a–d for a brief description of the prior art technology associated with computed tomography (CT) scanning. FIG. 1 shows a perspective view of one of the most commonly utilized applications of CT technology in medical research and patient imaging. As shown in FIG. 1, the standard CT scanner (10) comprises a stationary frame work (12) within which a rotating torodial scanning cylinder (14) is mounted. The patient (16) (or other object in other applications) is placed on a linear track (18) that directs patient (16) into the central open area (20) of the cylindrical scanning cylinder (14). X-ray source (22) is mounted in a stationary position within rotating scanning cylinder (14). Opposite X-ray source (22) across the open portion of scanning cylinder (14) is a single X-ray detector (24) or an array of detectors not shown in other applications.

In this most simple system described in FIG. 1, scanning cylinder (14) rotates about stationary patient (16) through a 90 degree ANGLE constantly scanning across a linear track (26a and 26b) equivalent to a diameter of the object under investigation. The various methods for scanning the object are described in more detail below with respect to FIGS. 2a–d. The typical application of the CT scanning device as shown in FIG. 1, however, is such that a number of "slices" of the object or patient (16) under investigation can be accumulated over time.

Again, however, the structure of the scanning device assumes a generally cylindrical cross section for the object or patient under scan. The relatively low length-to-width ratio of the human body (at least in cross sectional area) and some other objects that have CT technology applied to them allows for fairly simple data collection and analysis and a fairly simple X-ray source and detection mechanism. Deviations from this generally cylindrical structure create the problems described above.

Figure 2A:
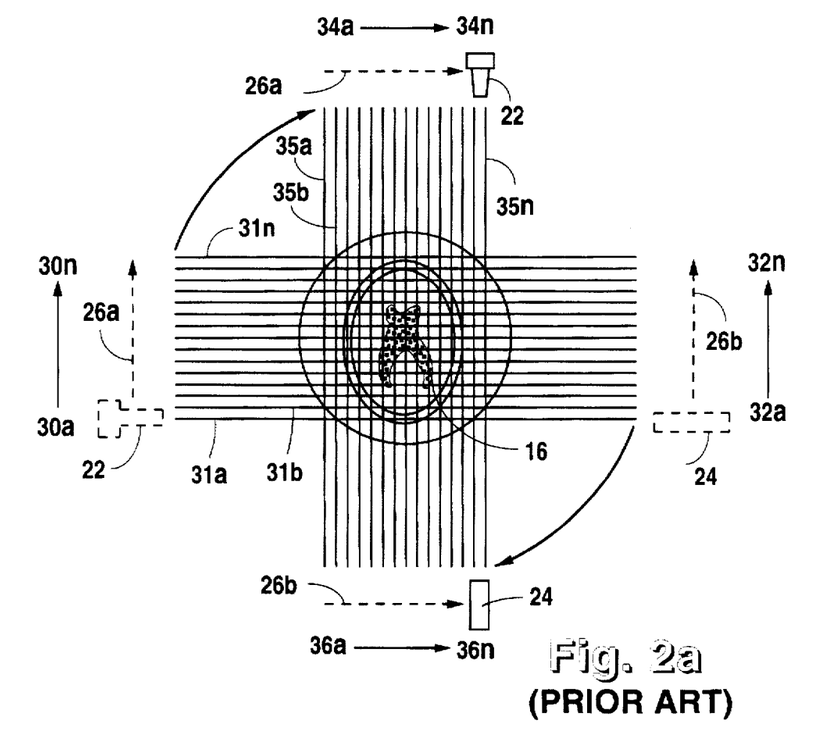
FIG. 2a is a schematic representation of a first scanning method for utilizing CT technology.

Reference is now made to FIGS. 2a–d for a brief description of a number of prior art scanning methods as they relate to the ability or inability to handle large length-to-width ratios in the cross sectional configuration of the body under investigation. FIG. 2a shows a scanning method typically applied in the device shown in FIG. 1, most often used in medical applications. X-ray source (22) is initially positioned at a first point (30a) to one side of object (16) under scan and directs an X-ray beam (31a) through a lower section of object (16) to detector (24) opposite on the other side of object (16) under investigation. X-ray source (22) and detector (24) then move linearly across a track (not shown) that establishes an X-ray beam (31b) generally parallel to beam (31a) and thereby progresses the X-ray beam across the entire diameter of object (16) under scan. Once this first pass (31a–31n) has been made across object (16), the entire scanning apparatus is rotated in one degree increments and a second scan or translation is made.

A large number of these scans are made each time with data being collected for each individual X-ray beam so as to produce an array of attenuation values that may, for example, be on the order of 20×90. The 20 dimension of the array would represent each of the independent X-ray beams (31a–31n) through a single translation of the device and the 90 dimension would represent each group of 20 values accumulated in a particular rotation increment. The result would be a large array of data that provides multiple attenuation values for each area or intersection within object (16) being inspected. Well known algorithms and standard means for reassembling this data thereafter recreate an image based upon variations in the attenuation values gathered.

Figure 2B:
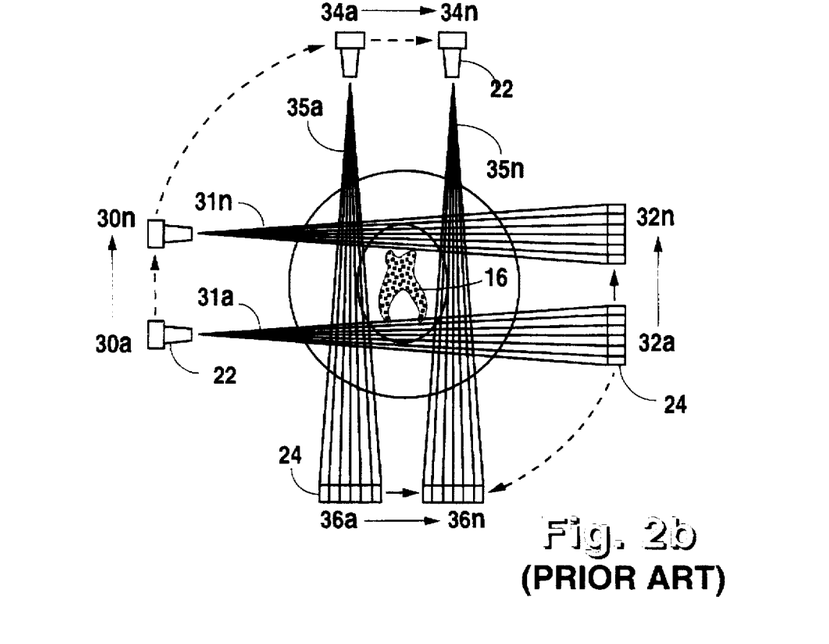
FIG. 2b is a schematic representation of a second scanning method for utilizing conventional CT technology.

Reference is now made to FIG. 2b for a second prior art method for utilizing CT technology. In this method, a non-collimated X-ray beam (31a) is directed across the object under investigation to an array of detectors (24) opposite it. This array of detectors (24) minimizes both the translational distance (30a–30n) that X-ray (22) source and detectors (24) must travel, and also minimizes the number of rotational increments that the entire scanning device must move through before completing a data image of the object. The system deviates from the first method shown in FIG. 2a by providing for multiple detectors (29a) to measure attenuation values from a single X-ray beam (31a) that passes through an area of object (16) under investigation. The entire X-ray source detector array assembly (24) still must rotate about object (16) and source (22) and detector (24) pair must still move across the diameter of object (16), but both of these processes are greatly accelerated because of the multiple detector configuration.

Figure 2C:
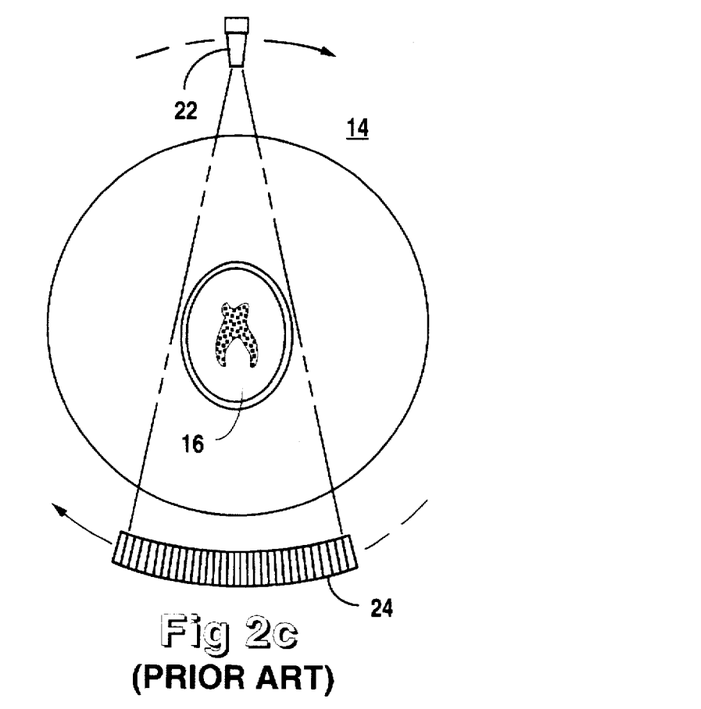
FIG. 2c is a schematic representation of a third scanning method for utilizing conventional CT technology.

Reference is now made to FIG. 2c for a description of a third standard means for utilizing CT technology in the examination of an object. In this method, a single X-ray source (22) is held "stationary" within rotating scanning device (14) and is directed across object (16) to a much larger array of X-ray detectors (24), typically high pressure xenon type detectors. Detector array (24) is typically configured in a semi-circular arc that minimizes deviations in total ray path from source (22) to detector (24). No translation of X-ray source (22) or detector array (24) across the diameter of object (16) is made. Rather, a constant incremental rotation of source (22)/detector array (24) is made that scans object (16) through each of the angles that the previous methods scan through. Again, an increase in the speed of imaging results from this system, but increased costs associated with the multiple detector array also result.

Figure 2D:
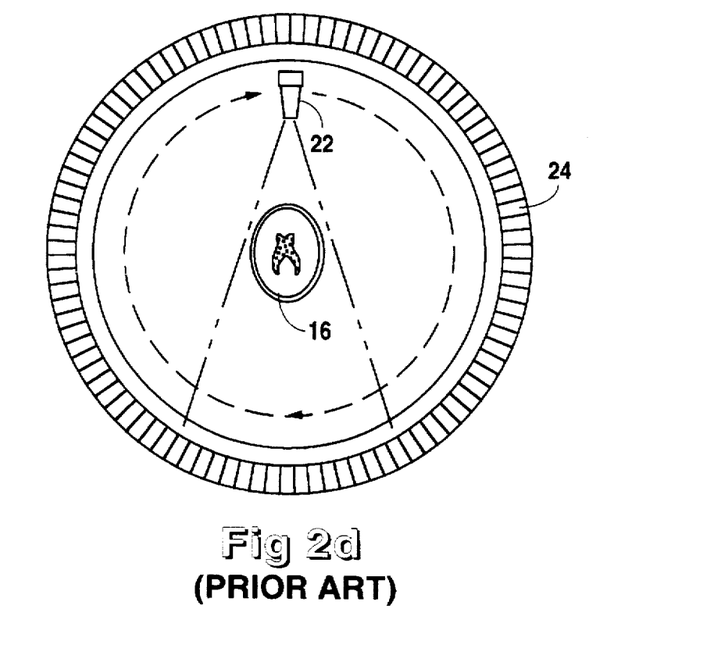
FIG. 2d is a schematic representation of a fourth scanning method for utilizing conventional CT technology.

Reference is now made to FIG. 2d for a brief description of a fourth method for implementation of standard CT technology. In this system, only X-ray source (22) rotates about object (16) under investigation and stationary detector array (24) that completely surrounds the cylindrical cross section of object (16) receives the X-rays in sequence as source (22) rotates. Here again, the speed of the scan is greatly increased, but the cost of the system likewise increases due to the necessity of having a larger detector array that completely surrounds the object under investigation.

Figure 3A:
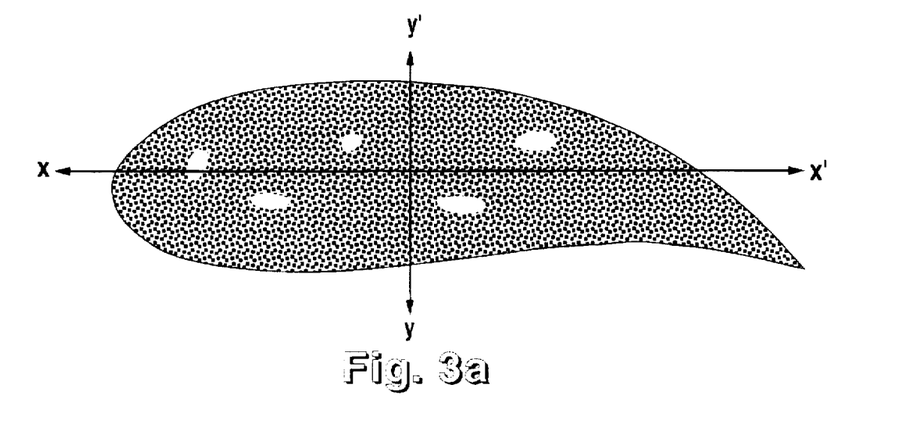
FIG. 3a is a cross sectional view of the actual structure of a turbine blade as might be investigated by either conventional CT technology or the process of the present invention.
Figure 3B:
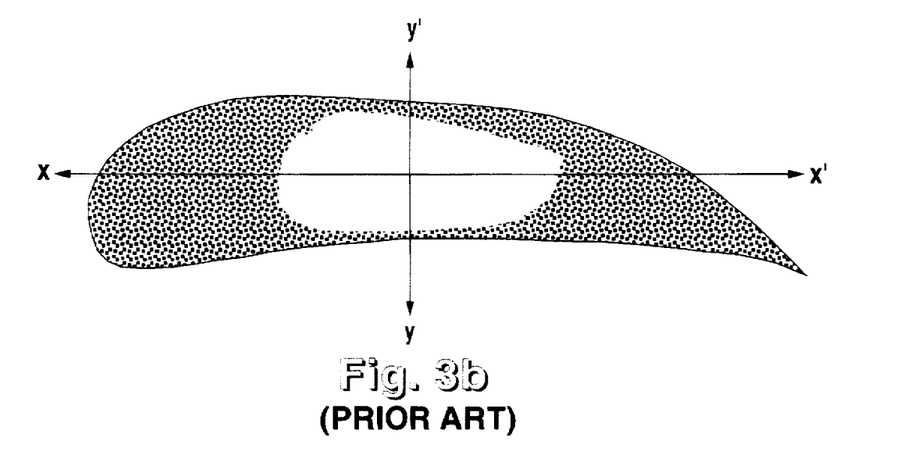
Figure 3C:
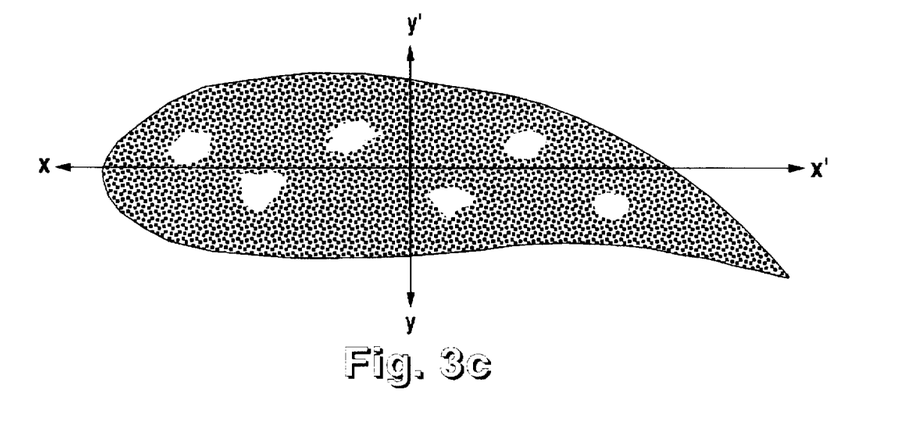

Reference is now made to FIGS. 3a–c for a detailed description of typical object images for which the process of the present invention would be advantageous. FIG. 3a shows a theoretical cross sectional view of a turbine blade with an array of internal fractures and voids similar to those that might result from prolonged fatigue and strain on the blade. It is noted that the cross sectional length X—X' is significantly greater than the cross sectional width Y—Y' and as such the travel path for an X-ray beam along X—X' through the turbine blade would be much greater than the path from along Y—Y' across the width of the turbine blade. This significant length-to-width ratio creates a cross sectional structure inappropriate for standard CT technologies. In this case, one part of a blade would absorb too much of the X-rays, while in the other directions across the width the blade might not absorb enough of the X-rays. This leads to underexposures and overexposures of the images that are generated.

Referencing FIG. 3b, a conventional CT scanner would with the above-described information create an image showing a large internal void or fracture because of its inability to compensate for the high length-to-width ratio of the cross section. As described earlier, the X-ray path from Y—Y' would likely result in an overexposed image (low attenuation) that would be created by an under absorbed X-ray beam. Even if the system averaged the cross sectional diameter of the object under examination, a greater absorption would be expected through the path from Y—Y' than would in reality be measured. Likewise, a lower absorption would be expected in the path from X—X' than would likely be measured. This results in the erroneous indications of the internal structure for the blade that are shown in FIG. 3b.

FIG. 3c represents a CT image of the internal structure of the turbine blade as might be determined by the method of the present invention. In this case, the reconstructed image is closer to that of the actual cross section because of the present invention's ability to appropriately compensate and adjust the X-ray energy and the detection timing. Taking into consideration the difference in the path length from Y—Y' from the path length from X—X' allows the system of the present invention to more accurately associate X-ray absorption with the actual internal characteristics of the turbine blade.

Figure 4:
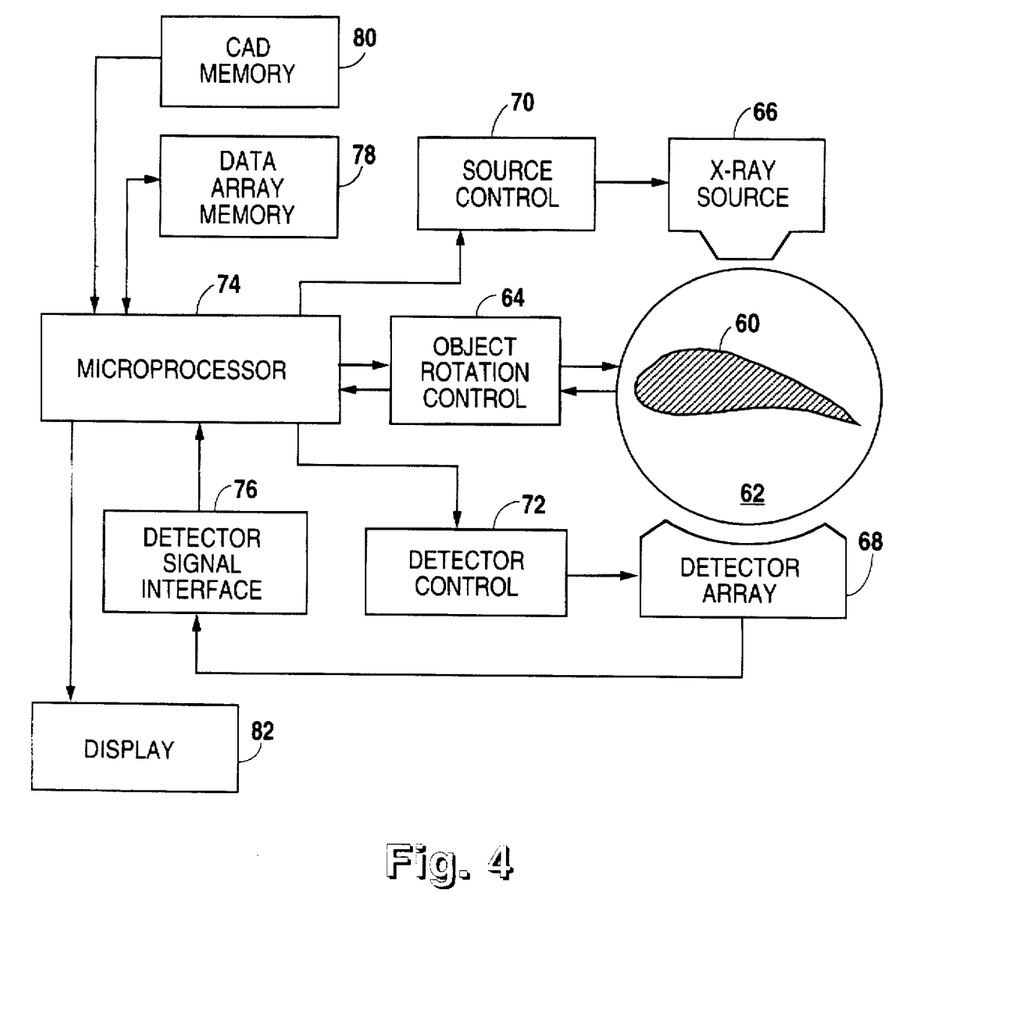
FIG. 4 is a schematic block diagram showing the various components necessary for implementation of the process of the present invention.

Reference is now made to FIG. 4 for a detailed description of a schematic diagram showing the essential elements necessary for implementing the process of the present invention. The hardware components of the system required for carrying out the steps of the procedures of the present invention are, to some extent, the same as those elements necessary for conventional CT scanning. One of the advantages of the present invention is that it can be implemented through the use of mostly standard CT equipment in conjunction with appropriate computer processing equipment capable of adding the computer aided design data to the analysis. FIG. 4 shows the unique configuration of components utilized to carry out the method of the present invention.

Object (60) under analysis is retained in some fashion inside rotating cylinder (62) in a manner that allows a scan to progress in any of the various ways already described above. It should be noted that the configuration of the apparatus of the present invention shown in FIG. 4 is schematic and is intended to show the functional relationships between the components rather than their physical location one adjacent to the other. The arrangement of X-ray source (66) and detector array (68), therefore, around object (60) and rotating cylinder (62) does not necessarily represent the physical appearance of the apparatus in operation.

X-ray source (66) directs a beam across object (60) retained in rotating cylinder (62) where it is received by detector array (68). The intensity of the X-ray beam generated by X-ray source (66) is controlled and varied by way of source control (70). In similar fashion, the integration time of detector array (68) is controlled and varied by detector control (72). In the preferred embodiment, both source control (70) and detector control (72) are, in fact, incorporated into the microprocessor control system utilized with typical CT scanning assemblies. Source control (70) and detector control (72) are shown as separate components for clarity in FIG. 4.

The intensity of X-ray source (66) and the integration time of detector array (68) are ultimately manipulated by microprocessor (74) through its instructions to source control (70) and detector control (72). Microprocessor (74) additional controls the position of object (60) by way of object rotation control (64). Through such control, microprocessor (74) is constantly aware of the rotational position of object (60) through feedback information from object rotation control (64).

Microprocessor (74) receives the X-ray beam attenuation signals from detector array (68) by way of detector signal interface (76). Microprocessor (74) controls X-ray source (66) intensity and detector array (68) integration time, depending upon information stored in CAD memory (80) relevant to the particular orientation of object (60) at any given point in the scan. With these variables set, a signal is detected by detector array (68) and conveyed to microprocessor (74) through detector signal interface (76) where the data is stored in data array memory (78).

After a complete scan is achieved, microprocessor (74), through fairly well-known algorithms and numerical analyses, manipulates data from data array memory (78) to create an image on display (82) of the cross sectional area of object (60) having been scanned.

Scanning with the above-described system can be carried out in any of the fundamental methods described previously in the application. The distinction between previous methods and the present invention lies in the incorporation of a processor capable of contributing the computer aided design data related to the object under investigation to the analysis of the X-ray attenuation.

The X-ray source and X-ray detector and their relationship to the object under investigation as shown in FIG. 4, therefore, is schematic only and it intended to be representative of any of a number of different CT configurations. It is expected that some rotation of the scanning system about the object under investigation would still be carried out much in the same way as described above, but the intensity and detection of the X-ray beam would be varied according to the rotational position of the scanning system. For example, if the object under investigation is longer in cross sectional dimension at an initial portion of the scan, the intensity of the X-ray beam would most appropriately be set higher than at a subsequent portions of the scan where the cross sectional dimensions of the object are smaller. In the alternative or in conjunction with variations in the X-ray beam intensity, modification of the integration time for the detector or the detector array could compensate for variations and absorption due to the significant length-to-width ratios seen.

Figure 5:
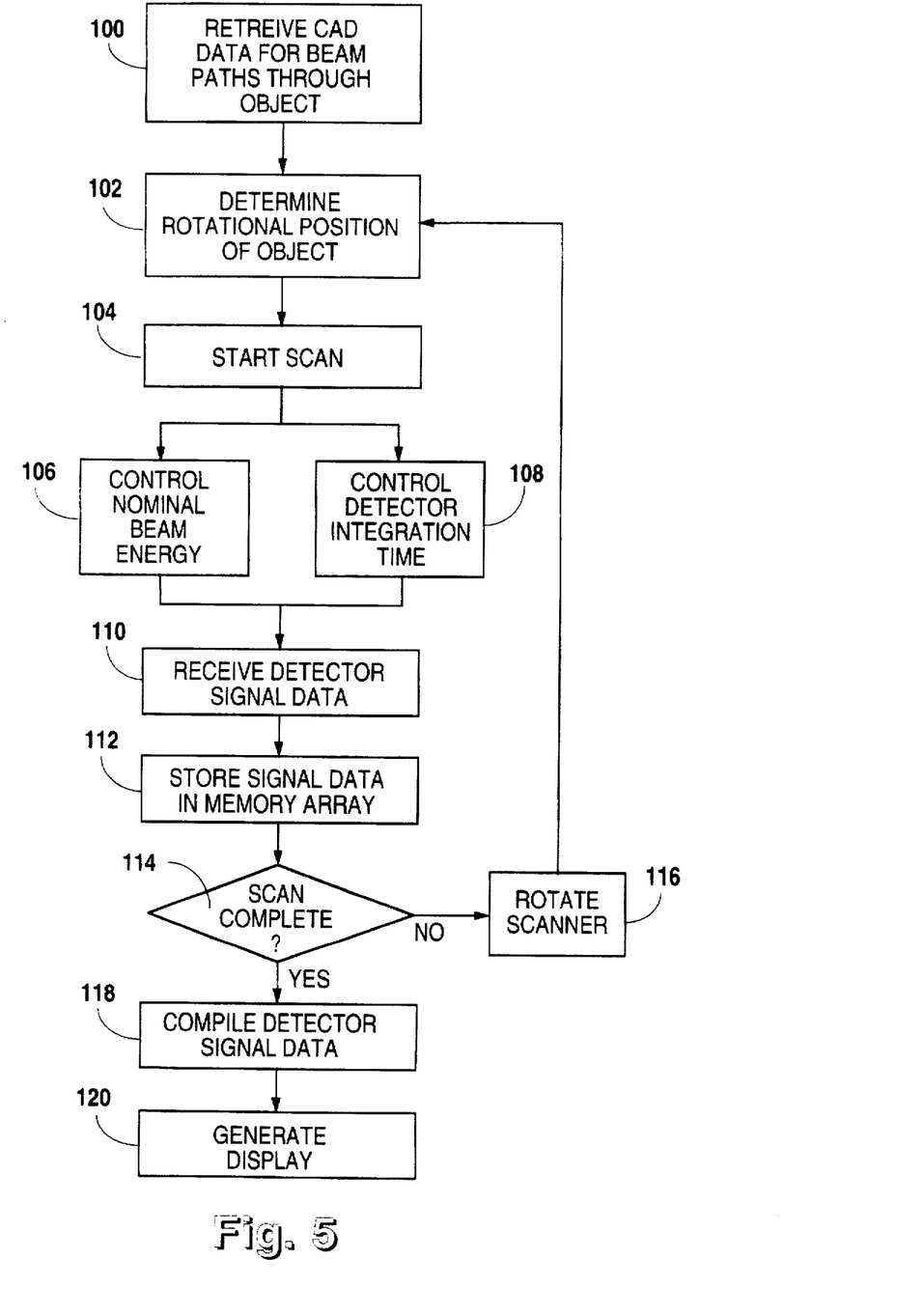
FIG. 5 is a flow chart of the various steps of the process of the present invention for use in a preferred embodiment.
Figure 9:
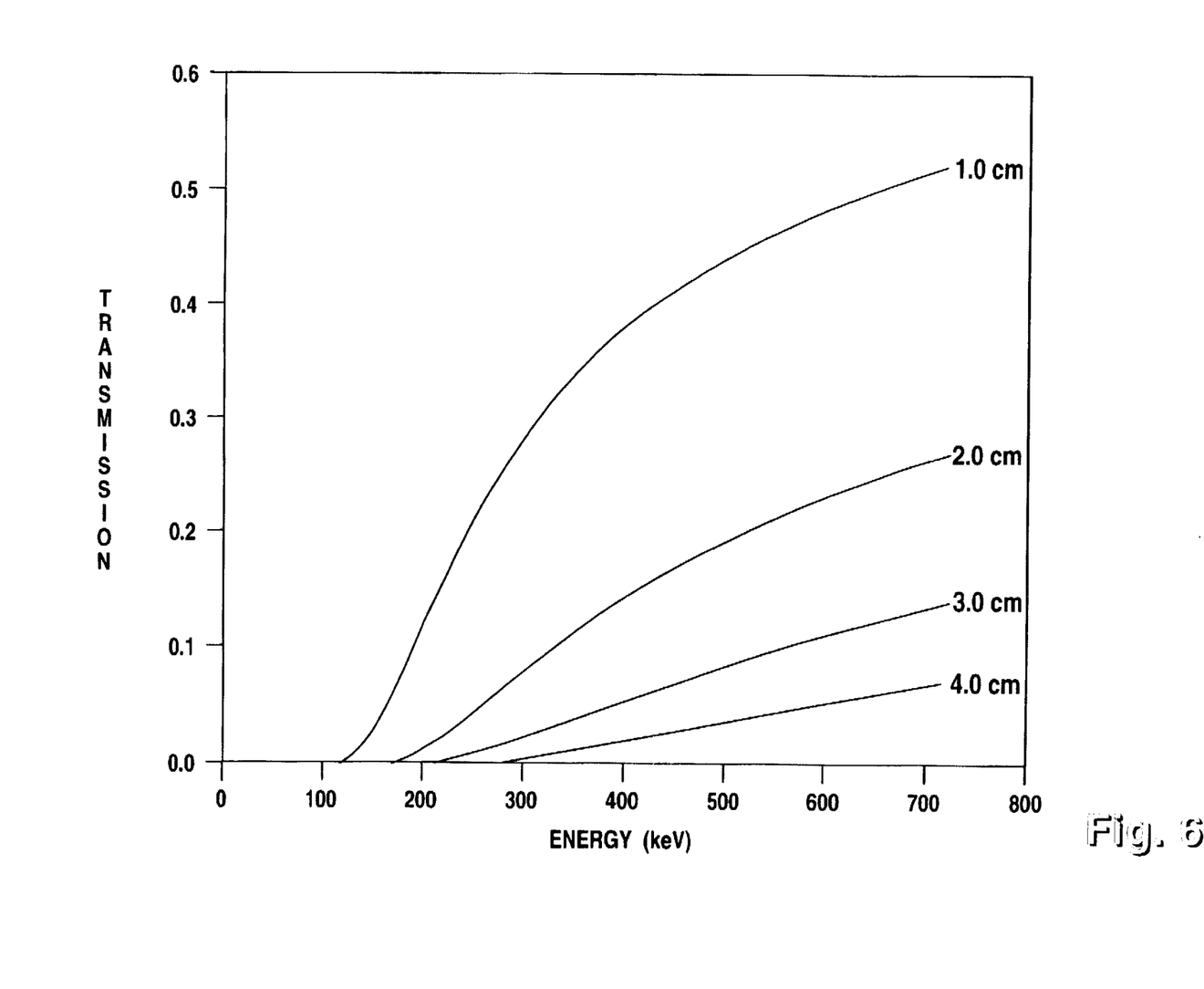

The process of the present invention would be carried out as is generally described in FIG. 5. Certain information derived from the computer aided design data for the object under investigation would be utilized to create a scan plan that incorporates not only positional variables with respect to the X-ray source and the detector array, but also power values necessary for controlling the intensity of the X-ray beam and time signals to control the integration timing of the detector array. The basic parameters involved in determining this scan plan would be a calculated beam path through the object at a particular orientation. With the computer aided design information, this calculated beam path could be easily determined and based upon the absorptive characteristics of the homogenous object, can be closely associated with a nominal absorption for those dimensions and that material. Once a nominal absorption is determined, it can be referenced to an appropriate X-ray intensity and an appropriate optimal integration time for the detector array. For example, the set of computer aided design data associated with a long dimension of a turbine blade might determine that the beam path through the object would be on the order of 8.5 cm. A similar patch across the width of a typical turbine blade might, for example, be only on the order of 1.5 cm. With this beam path determination, an increase in the intensity and/or an increase in the integration time of the detector array would allow the electronically created image that results at to create a reference, contrast, and resolution that might be associated with a nominal, homogenous internal structure. Any inclusions, fractures, voids, etc., in the internal structure, therefore, would create an appropriate deviation from the nominal contrast and resolution that would show up as an appropriate value in the detector image. Effectively, the computer aided design data would establish references, contrasts, and resolutions for the entire object and/or the entire scan associated with the varying rotational increments. Once these reference values have been established for each scan, appropriate modifications of the X-ray energy level and the integration timing for the detectors at each position would be communicated to the X-ray source and the detector array. This effectively creates a gray background image upon which variations of interest can be plotted or created according to deviations in the absorption or attenuation from the expected and calculated nominal absorptions and attenuations.

Reference is made to FIG. 5 for a detailed description of the fundamental sequence of steps carried out by the method of the present invention. At the initial scanning start step (100), the object to be scanned is positioned within the appropriate hardware scanning system; and the relevant CAD data pertaining the object is loaded into the microprocessor memory. Next, at step (102), the rotational position of the object is initially determined so that in step (104) the appropriate CAD data, for a beam passing through the object at that orientation, can be retrieved from CAD memory. This information includes the beam path length anticipated and the existence of any non-homogenous features in the background structure of the object.

With this information, the microprocessor determines an appropriate combination of X-ray source beam intensity and detector array integration time. In step (106) microprocessor controls the nominal beam intensity appropriate for the beam path anticipated and, in step (108), controls the detector integration time optimal for receiving such beam intensity.

The detector array, in step (110), then receives the X-ray beam and transmits a detected attenuation signal back to the microprocessor. In step (112), the microprocessor stores the signal data received, generally without analysis or manipulation at this point, in its memory arrays. In step (114), the microprocessor determines whether or not the scan is complete based upon a full rotation/translation handling of the object. If the scan is not complete, the microprocessor in step (116) rotates the scanning array the specified increment and then proceeds again to step (102) wherein the rotational position of the object is determined. This circuit from step (102) through step (116) is repeated until such time as the microprocessor determines from the accumulation of data that the scan is complete. At that point, in step (118), the microprocessor compiles the detector signal data previously stored in its memory arrays. Again, through analyses and methods well known in the CT technology field, microprocessor assembles the data to create an image that, in step (120) it generates on a display.

The image thus displayed will appear to those skilled in the field to be similar in many respects to standard CT technology images, but would represent a more accurate indication of the internal cross-sectional structure of the object under investigation because of the system's ability to anticipate the geometry and non-homogenous structure of the object in a manner that compensates for large length-to-width ratios in the cross section. Thus, as described above with respect to FIGS. 3a–3c, the images presented, though not immediately distinct from previously-obtained CT scan images, allows a more accurate understanding of the internal structures of objects under investigation by test operators viewing these images on the displays.

Again, it is understood that the apparatus of the present invention and the method associated with implementing the system can function in conjunction with a number of different CT scanning methods without deviation from the contemplated scope. Other CT scanning methods, not specifically mentioned herein, could also incorporate the method of the present invention through simple modifications of the microprocessor systems that control the scanning devices. As long as the X-ray or other radiation source can be modified in intensity and/or the appropriate detector array can be modified in its sensitivity through integration time or otherwise, the process or the present invention can be implemented.

Insofar as many objects normally subjected to such CT scanning procedures already have accurate CAD data associated with their structures, the process of providing such data to the microprocessor for control of the scan plan and for later analysis, generally presents no significant problems. Even without such CAD data already in hand, however, most objects can be generically described in cross sectional structure with sufficient clarity that basic CAD data arrays can be created with little effort. Since it is typically the length-to-width ratios that are of concern in creating accurate scan image data, geometric variations in the cross section that are small in comparison to either the width or length of the object are generally irrelevant and need not be part of the CAD data utilized by the present system.

It is also anticipated that a second preferred embodiment of the present invention that differs in a single, significant manner from that described above would become apparent to those skilled in the art. Since the microprocessor described in the present invention is capable of taking CAD data and utilizing it to determine a nominal scan beam and thereby control an X-ray source and a detector array to optimally create and receive that beam, it is anticipated that the microprocessor could also receive signal data based upon a fixed beam and then infer attenuation modifications from the CAD data. In other words, rather than anticipating the internal structure of the object being scanned and modifying the beam prior to its transmittal through the object, the system of the present invention could simply receive the signal data associated with the fixed beam intensity and thereafter modify the attenuated signal according to the CAD data stored for that particular beam path. To some extent, this approach would simplify the apparatus of the present invention insofar as fixed X-ray sources and detector arrays could be utilized. This approach would increase the processing requirements for analyzing the signal once the scan is complete. Any attenuated signal received and stored by the system would be qualified and modified by some amount, depending upon the CAD data information for the beam path associated with that signal.

While this approach would, theoretically, be able to match the imaging of the earlier described method, the practical application, and the systems available in current CT technology, permit and make more advantageous the establishment of nominal beams based upon the known cross-sectional structure of the object being scanned. Nonetheless, under certain circumstances, it is anticipated that the second approach might be more practical.

While the present invention has been described in both apparatus and method in a number of specific forms, these descriptions are not intended to be limiting of the scope of the invention. Reference is now made to the appended claims for a more definite description of the specific elements that define the scope of the present invention.

We claim:

1. An apparatus for optimizing computer tomography images from standard computer tomography scanning devices comprising:

a scanning radiation source;

a scanning radiation detector;

means for controlling an intensity of radiation directed from said scanning radiation source;

means for controlling a sensitivity of said radiation detector;

means for controlling a rotational position of an object to be scanned; and microprocessor means for directing the control of said scanning radiation source, directing the control of said radiation detector, and directing the control of said rotational position of said object being scanned, said microprocessor comprising first means for retaining data indicative of a geometric, cross-sectional structure of said object being scanned, said geometric data having been previously established and provided to said microprocessor, said microprocessor further comprising second memory means for storing information associated with radiation beam intensity received by said radiation detector;

wherein said microprocessor utilizes said geometric data in said first memory means to vary said intensity of said radiation from said radiation source and to vary said sensitivity of said detector array in a manner that provides a nominal radiation beamed through said object being scanned, and, thereafter, said microprocessor being capable of assembling a cross-sectional image of said object from said stored information after a complete scan of said object.

2. The apparatus of claim 1 wherein said radiation source comprises an X-ray radiation source and said radiation detector comprises an X-ray detector array.

3. The apparatus of claim 1 wherein said radiation source control means and said radiation detector control means are incorporated into said microprocessor means.

4. The apparatus of claim 1 wherein said radiation source and said radiation detector are positioned so as to rotate about said object being scanned under control of said microprocessor.

5. The apparatus of claim 1 wherein said object being scanned is positioned so as to be rotated between said radiation source and said radiation detector, said radiation source and said radiation detector being fixed in position with respect to said apparatus.

6. A method for optimizing computer tomography images from standard computer tomography scanning devices comprising the steps of:

compiling an array of data descriptive of a cross-sectional geometry of an object to be scanned;

storing said geometric data array in a memory means accessible by a microprocessor;

positioning an object to be scanned within a scanning means, said scanning means comprising a radiation source and a radiation detector;

identifying a reference position of said object being scanned;

associating elements of said geometric data array with said identified position of said object being scanned;

determining an appropriate modification of a nominal radiation beam intensity to be directed through said object being scanned for said identified position, said modified nominal beam being of an intensity that compensates for deviations in dimensional and structural characteristics of said object along identified beam path;

controlling a nominal beam intensity;

controlling a nominal detector sensitivity;

receiving a detector signal indication of an attenuation of said radiation beam;

storing said detector signal in a memory means;

repositioning said object being scanned and repeating said steps associated with controlling beam intensity and detector sensitivity and receiving a new detector signal for said new rotational position; and upon completion of said scan compiling said stored detector signal data into an image indicative of an internal cross-sectional structure of said object being scanned.

* * * * *